US006901285B2

(12) United States Patent
Schreck

(10) Patent No.: US 6,901,285 B2
(45) Date of Patent: May 31, 2005

(54) SYSTEM AND METHOD FOR SYNTHESIZING LEADS OF AN ELECTROCARDIOGRAM

(76) Inventor: David M. Schreck, 80 Division Ave., Summit, NJ (US) 07901

( * ) Notice: Subject to any disclaimer, the term of this patent is extended or adjusted under 35 U.S.C. 154(b) by 0 days.

(21) Appl. No.: 10/150,719

(22) Filed: May 17, 2002

(65) Prior Publication Data

US 2003/0216655 A1 Nov. 20, 2003

(51) Int. Cl.[7] ............................................. A61B 5/0402
(52) U.S. Cl. ...................................................... 600/509
(58) Field of Search ................................. 600/508, 509, 600/511, 512

(56) References Cited

U.S. PATENT DOCUMENTS

| | | | |
|---|---|---|---|
| 4,850,370 A | * | 7/1989 | Dower ........................ 600/512 |
| 5,058,598 A | | 10/1991 | Nicklas et al. |
| 5,318,037 A | | 6/1994 | Evans et al. |
| 5,377,687 A | | 1/1995 | Evans et al. |
| 5,711,304 A | | 1/1998 | Dower |
| 6,119,035 A | | 9/2000 | Wang |

OTHER PUBLICATIONS

B.A. Menown, J. Allen, J. McC. Anderson, and A.A.J. Adgey, "ST Depression Only on the Initial 12–Lead ECG: Early Diagnosis of Acute Myocardial Infarction," European Heart Journal vol. 22, Issue 3, Feb. 3, 2001, pp. 218–227.
E. Frank, "An Accurate, Clinically Practical System for Spatial Vectorcardiography," Circulation, vol. XIII, May 1956, pp. 737–749.
E. R. Malinowski and D. G. Howery, *Factor Analysis in Chemistry*, Wiley–Interscience Publication, John Wiley & Sons,1980, pp. 10–58, Appendix 1 "Factor Analysis Mathematical Treatment," Appendix 2 "Cumulative % Sum of theEigenvalues as a Method to Identify Number of Factors," Appendix 3 "Theory of Factor Analysis as Data ImprovementTechnique".

M. J. Katz, "Fractals and the Analysis of Waveforms," from "Comput. Biol. Med." vol. 18, No. 3, pp. 145–156, 1988 (Pergamon Press).

C.L. Shavers, M.L. Parsons, and S.N. Deming, "Simplix Optimization of Chemical Systems," Journal of Chemical Education, May 1979, vol. 56, pp. 307–309.

Schreck DM, et al: Derivation of the 12–lead electrocardiogram using abstrat factor analysis and simplex optimization. Int J Bioelectromagnetism; 4(2):337–338. Dec. 11, 2002.

F. C. Moon, Chaotic and Fractal Dynamics, An Introduction for Applied Scientists and Engineers, Wiley–Interscience Publication, Published 1992 by John Wiley & Sons, Inc., pp. 325–341.

* cited by examiner

*Primary Examiner*—George R. Evanisko
(74) *Attorney, Agent, or Firm*—Greenberg Traurig, LLP; Eugene C. Rzucidlo; Beverly W. Lubit

(57) ABSTRACT

A method for synthesizing electrocardiogram leads includes obtaining a sequence of voltage-time measurements for a set of electrocardiogram leads and subjecting the measurements to abstract factor analysis to obtain a set of eigenvalues and associated eigenvectors. A minimal subset of electrocardiogram leads is identified from which the voltage-time measurements can be calculated with acceptable error. Simplex optimization is performed on a subset of the voltage-time measurements measured with the minimal subset of electrocardiogram leads to obtain a universal transformation matrix, and the universal transformation matrix is multiplied by the subset of the voltage-time measurements to calculate the full set of voltage-time measurements. The full set of leads can be used to calculate a body surface map, and the eigenvalues can be tracked in time to predict the onset of pathology such as myocardial infarction.

24 Claims, 14 Drawing Sheets

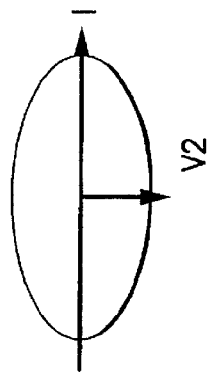
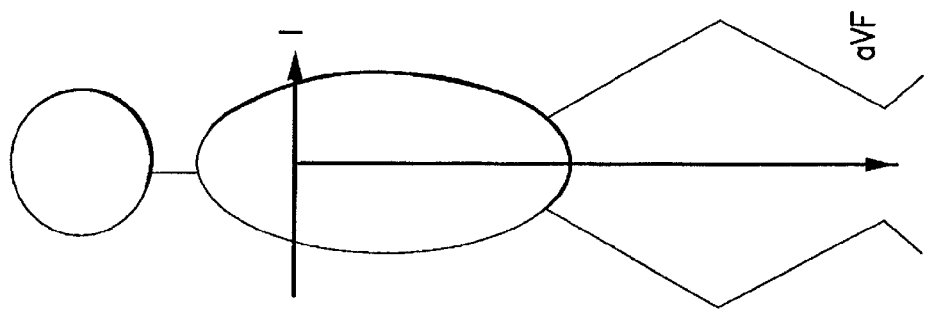
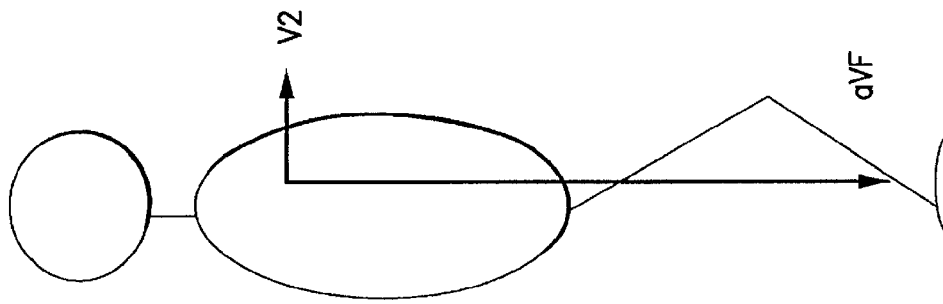

SYSTEM AND METHOD FOR SYNTHESIZING LEADS OF AN ELECTROCARDIOGRAM

FIELD OF THE INVENTION

This invention is directed to synthesizing the leads of an electrocardiogram ("ECG") from three measured leads belonging to the set of routinely used leads, including the standard 12-lead ECG, and to visually present a body surface map ("BSM") based on an n-lead ECG that is derived from three measured leads, and to predict the development of pathology, including acute myocardial infarction (more commonly known as a "heart attack") using the calculation of the ECG eigenvalues.

BACKGROUND OF THE INVENTION

The ECG is a record of the electrical activity of the heart that is a commonly used diagnostic screening test in many medical settings. The standard ECG record includes 12 lead waveforms, denoted as I, II, III, aVR, aVL, aVF, V1, V2, V3, V4, V5, and V6, arranged in a specific order that is interpreted by a physician using pattern recognition techniques. The ECG is acquired by specially trained technicians using specialized hardware and equipment. In the usual configuration, 10 electrodes are placed on the body torso to measure the electrical potentials that define the standard 12 leads. Other lead systems have been tested over the years. These include the Frank vectorcardiogram ("VCG") system, which uses 3 nearly orthogonal leads denoted as X, Y, and Z; 4 right chest leads, denoted by V3R, V4R, V5R, and V6R; and 3 left posterior leads, denoted as V7, V8, and V9. No single manufacturer currently makes equipment that allows for the acquisition of all 22 leads. In order to acquire these leads, the technician must first remove the lead clips attached to the standard electrode placement sites and then re-attach them on the electrodes placed on the non-conventional sites. This requires at least 3 separate tracing acquisitions and a total of 21 electrode placements.

It is usual in the practice of medicine to place patients with potential cardiac abnormalities on a rhythm monitor, a specially designed hardware equipment that displays only one ECG lead but which has the capability of measuring 3 different leads. There are some manufacturers who have designed rhythm monitors that can display three leads as well but the usual display format is still one lead. With this equipment, the patient has 3 to 4 electrodes placed on the body torso to acquire the 3 different lead configurations. While the patient is connected to the rhythm monitor, if a standard 12 lead ECG is ordered, the technician will then place all of the additional electrodes for the separate acquisition of the ECG. Thus, the efficiency of acquiring an ECG would be improved if there existed a process by which the standard 12 lead ECG, the 3 lead VCG, the 4 right chest leads, or the 3 left posterior leads could be acquired instantaneously on demand from the rhythm monitor rather than the usual ECG machine, using fewer than standard number of electrodes.

Nicklas, et al., in U.S. Pat. No. 5,058,598, invented a system for synthesizing ECG leads based on developing a patient-specific transform. This system could synthesize a 12 lead ECG based on receiving data from 3 leads. However, this system required first acquiring a complete n-lead ECG from a patient in the usual manner in order to compute a patient specific transformation, which would then be applied subsequent ECG data acquired from that patient. This is cumbersome, as the resulting transformation is applicable to only one patient and needs to be stored in a medium that must be accessible for use during the patient's hospital stay. In addition, the Nicklas transformation may also have a time dependency, indicating that the patient transform may change with time such that the transformation may need to be re-computed for each subsequent encounter with that patient for diagnostic accuracy.

Dower, in U.S. Pat. No. 4,850,370, used the Frank VCG 3 lead system to derive the 12 lead ECG, however, this system is not conventional and is unfamiliar to most clinical staff. Dower also developed another unconventional lead configuration known as the EASI system, but this configuration requires the acquisition of 4 leads to derive the 12 lead ECG.

SUMMARY OF THE INVENTION

The present invention solves the aforementioned problems by using the mathematical techniques of abstract factor analysis and the simplex optimization algorithm to derive a universal transformation matrix that is applicable to all patients and is independent of time. This universal transformation matrix is thus applicable when needed and does not require the acquisition of a complete n-lead ECG for each patient prior to its implementation.

In order to do this, one first measures and digitizes the voltage-time data for some set of ECG leads to define an ECG training set. Without limitation, examples of lead sets include the following formats:

12 leads: I, II, III, aVR, aVL, aVF, V1, V2, V3, V4, V5, V6;
15 leads: I, II, III, aVR, aVL, aVF, V1, V2, V3, V4, V5, V6, X, Y, Z;
15 leads: I, II, III, aVR, aVL, aVF, V1, V2, V3, V4, V5, V6, V7, V8, V9;
16 leads: I, II, III, aVR, aVL, aVF, V1, V2, V3, V4, V5, V6, V3R, V4R, V5R, V6R;
18 leads: I, II, III, aVR, aVL, aVF, V1, V2, V3, V4, V5, V6, V7, V8, V9, X, Y, Z;
19 leads: I, II, III, aVR, aVL, aVF, V1, V2, V3, V4, V5, V6, V7, V8, V9, V3R, V4R, V5R, V6R;
22 leads: I, II, III, aVR, aVL, aVF, V1, V2, V3, V4, V5, V6, V7, V8, V9, V3R, V4R, V5R, V6R, X, Y, Z.

Once the voltage-time data arrays have been acquired, the abstract factor analysis ("AFA") technique is applied to each ECG voltage-time data array in a training set in order to minimize the error in the measured arrays. The final step is then to apply the simplex optimization technique ("SOP") to the training set in order to derive a universal transformation matrix applicable to all patients, and is time independent. This universal transformation matrix can then be applied to a standard measured 3 lead subsystem to derive the standard 12 lead ECG as well as other systems, and can generate at least 22 leads to enable a more accurate interpretation of cardiac electrical activity. These derived ECG values are approximately 99% accurate when compared to observed lead measurements. The standard 3 lead system used to synthesize the 12 lead ECG are the measured I, aVF and V2 leads that belong to the standard 12-lead system. This measured lead set is conventional and familiar to clinical staff and are thus easy to apply. Since this lead set approximates an orthogonal system, these lead vectors can be plotted against each other in a 3-dimensional space to yield a space curve whose properties can be correlated with coronary pathologies. In addition, it is theoretically possible to use the universal transformation matrix of the invention to generate an n-lead ECG, where n is arbitrarily large.

The techniques of abstract factor analysis and simplex optimization are well known in the applied mathematical art. For abstract factor analysis, see, e.g., E. R. Malinowski, *Factor Analysis in Chemistry*, 2ed., John Wiley & Sons, New York, 1991. For simplex optimization, see, e.g., C. L. Shavers, M. L. Parsons, "Simplex Optimization of Chemical Systems", *Journal of Chemical Education* 56:307, May 1979.

BRIEF DESCRIPTION OF THE DRAWINGS

FIG. 9a is a schematic representation of a sagittal view of the placement of the aVF and V2 leads on a human torso.

FIG. 9b is a schematic representation of a frontal view of the placement of the aVF and I leads on a human torso.

FIG. 9c is a schematic representation of a transverse view of the placement of the I and V2 leads on a human torso.

DETAILED DESCRIPTION OF THE INVENTION

Figure 5:
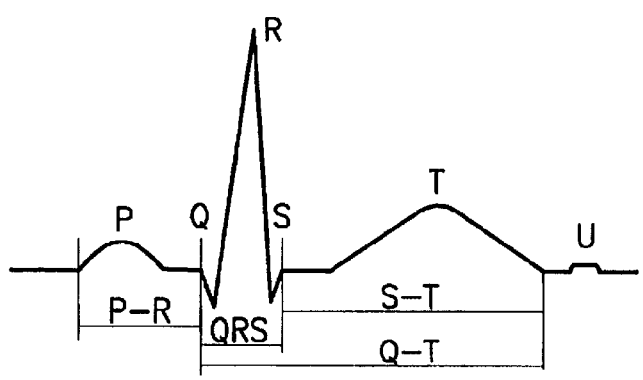
FIG. 5 depicts a typical cardiac electrical cycle as measured by an ECG.

The full cycle of cardiac activity is represented by a wave known as the PQRST wave, defined by Einthoven, *Arch. ges Phys*. 150:275, 1913, reprinted in *Am. Heart J*. 40:163, 1950, translation by H. E. Huff and P. Sekelj. This wave represents full contraction and relaxation of the heart. An example of a PQRST wave is shown in FIG. 5. One complete heart cycle averages $\frac{1}{72}$ seconds.

Figure 1:
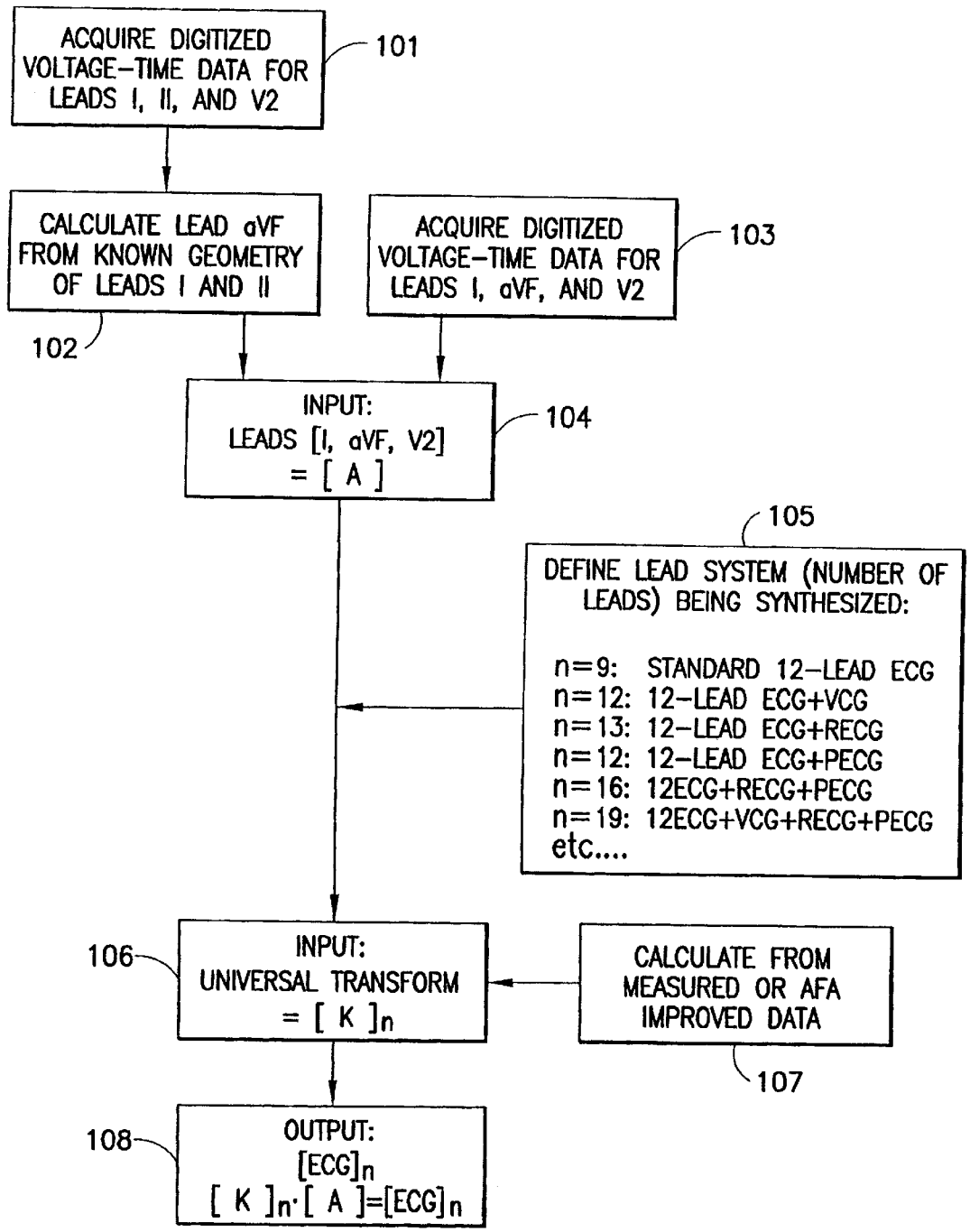
FIG. 1 depicts a flow diagram of how the universal transformation matrix of the present invention is calculated and used.

A flow chart illustrating the overall process of synthesizing and using the universal transformation matrix of the invention is depicted in FIG. 1. The first step, shown in block 101, is to acquire a sequence of digitized voltage-time data for one complete cycle for leads I, II, and V2. Multiple data sets can be acquired, and each set typically contains upward to 300 measurements. From the known geometry of leads I and II, lead aVF can be calculated in block 102. The formula for generating lead aVF from leads I and II is shown at step 202 of FIG. 2. Alternatively, a sequence of digitized voltage-time data for leads I, aVF and V2 can be measured directly, as indicated in block 103. Leads I, aVF and V2 are members of the set of leads that make up the standard 12-lead ECG and are very well known to clinical staff. The sequence of digitized voltage-time measurements forms a matrix [V], which is a 3×M matrix, where M is the number of measurements in time, as indicated in block 104. Typically, 300 sequential time measurements are taken.

Figure 10:
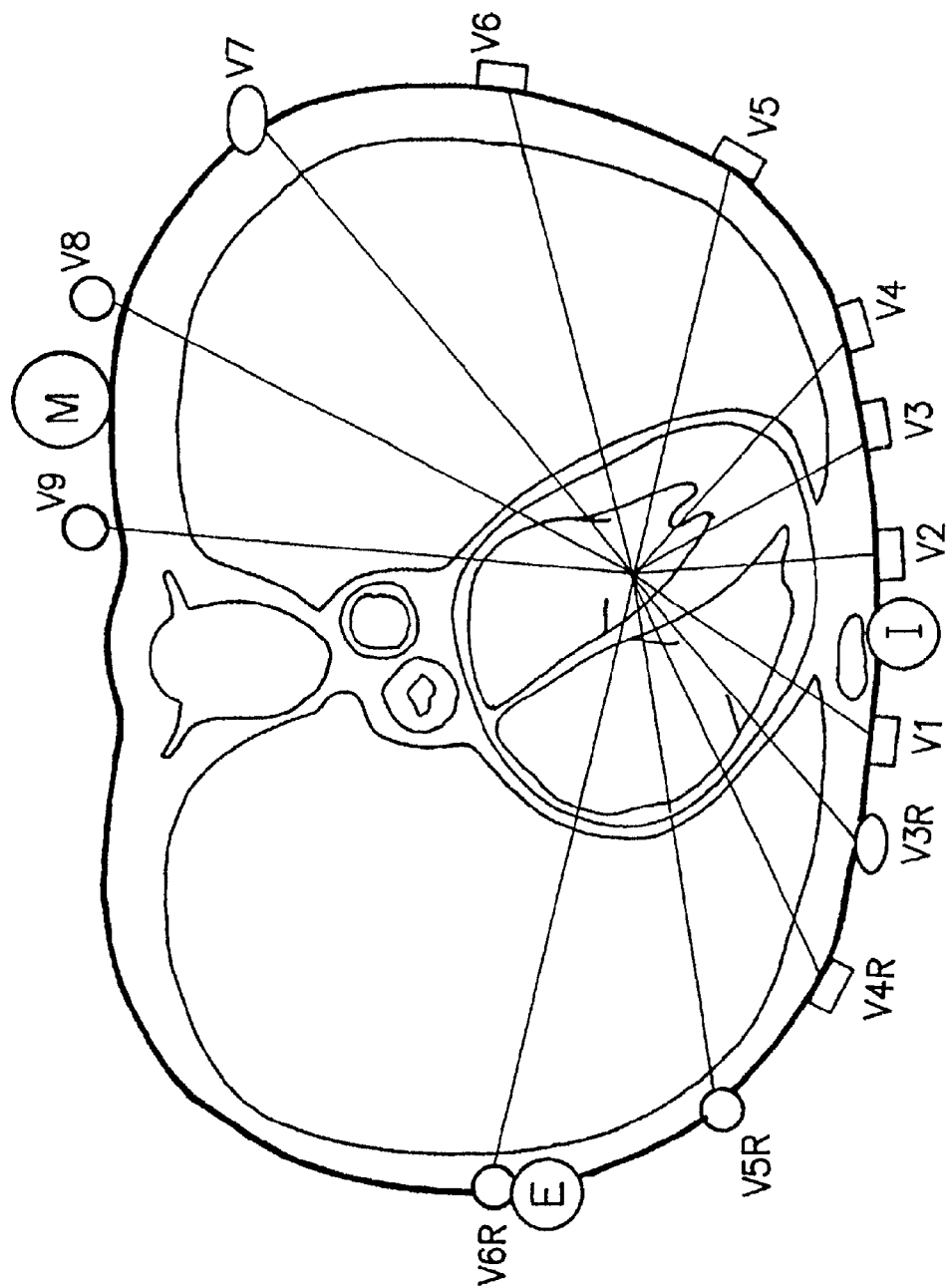
FIG. 10 depicts a transverse planar cutaway view of a human torso showing placement of the 13 V leads and the 3 Frank leads.
Figure 11:
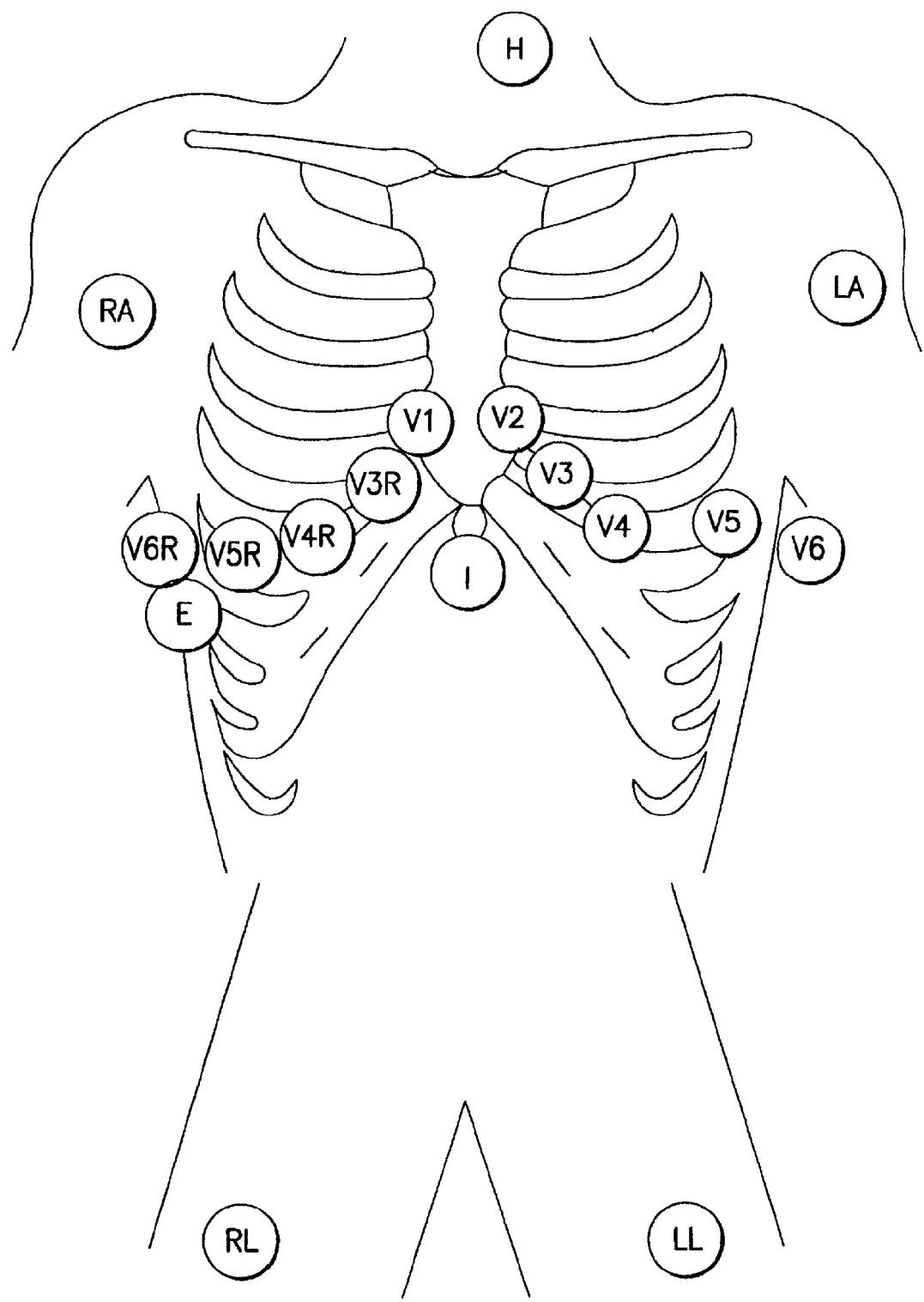
FIG. 11 depicts a frontal cutaway view of a human torso showing placement of the leads of FIG. 10.

The placement of leads I, aVF, and V2 on a human body is schematically illustrated in the three views depicted in FIG. 9. These views are, respectively, a sagittal view, a frontal view, and a transverse view. This lead set was chosen for the following reasons. As stated, these leads are well known to clinicians, nurses and ECG technicians. There is no need to place these leads on places that are unconventional, thus there is no need to research, develop and validate a new, unconventional lead configuration. In addition, these leads are approximately orthogonal. Any of the other 22 leads discussed above can be derived from the lead set of I, aVF, and V2. FIG. 10 depicts transverse planar view of the placement of the 13 V-leads (V1–V9, V3R–V6R) and the 3 Frank (X, Y, Z) leads (labeled as I, E, and M, respectively, in the drawing figure) of the 22-lead set that can be predicted from the measured lead set. A frontal view of the lead placements of FIG. 10 is shown in FIG. 11, which also depicts placements for leads RA, LA, RL, and LL. A total of 21 electrodes must be placed to capture the voltage-time data for 22 leads. The system of the present invention requires the placement of only 4 or 5 electrodes (depending on the design of the grounding electrode) to capture 3 leads from which the other 19 leads are derived. This has the advantages of cost savings, speed, minimizing errors from lead placement variability, and efficiency, particularly when sequential tracings are needed.

Abstract Factor Analysis

Figure 2:
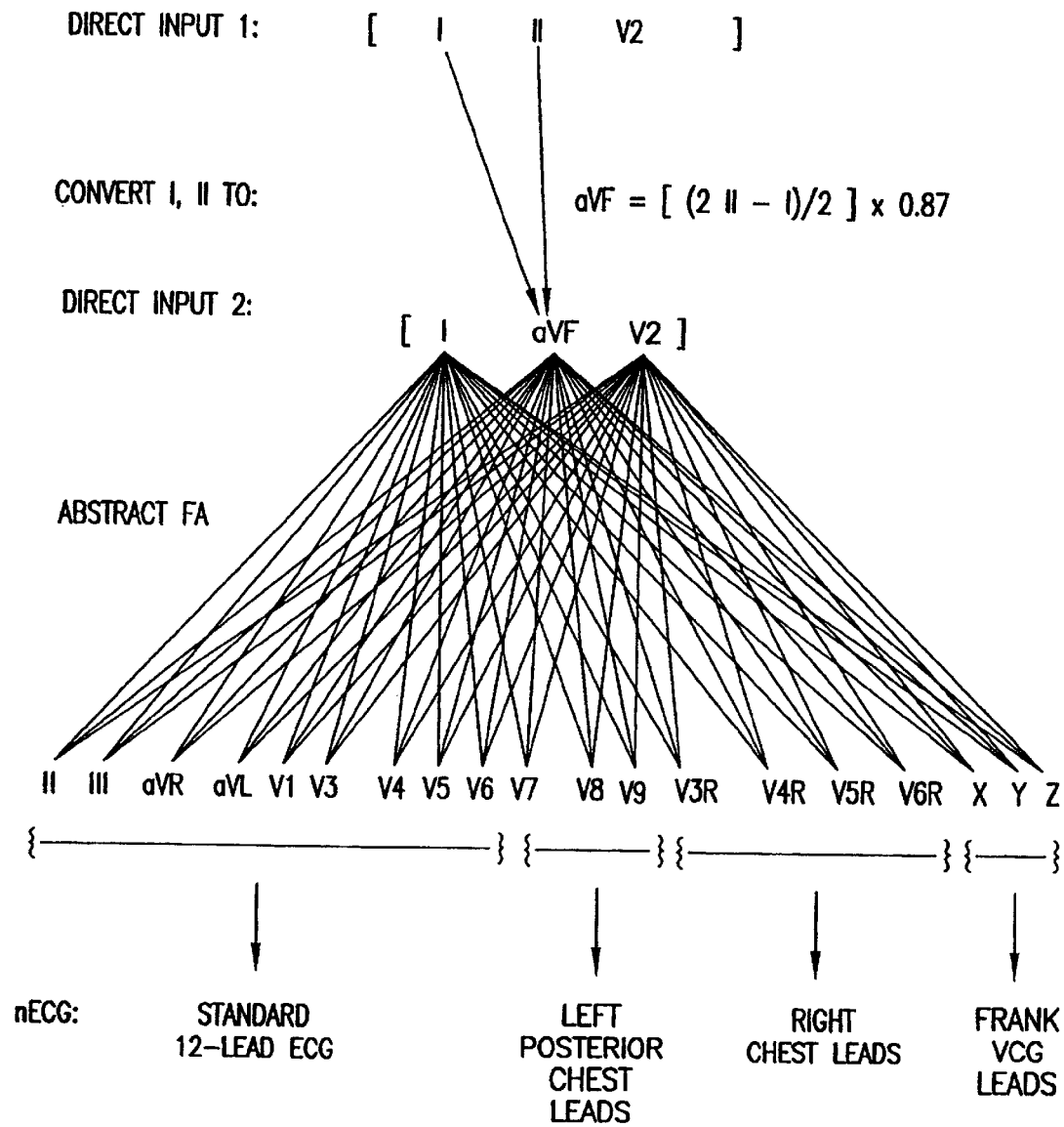
FIG. 2 depicts how the various n-lead systems are formed from combinations of 3 leads.
Figure 3:
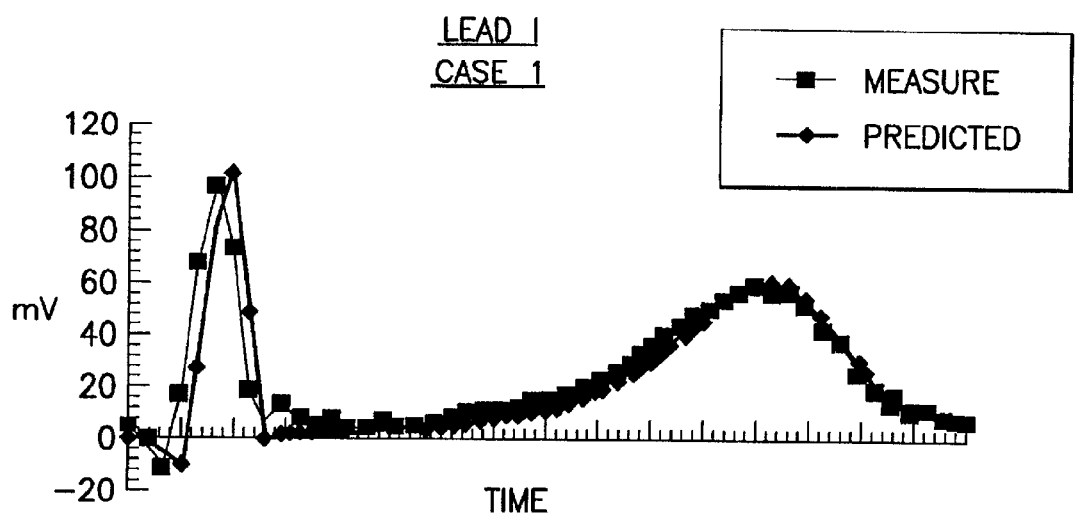
FIG. 3 depicts a comparison of a measured ECG against one predicted by the application of the universal transformation matrix of the invention.

Abstract factor analysis ("AFA") is applied to the entire n-lead ECG measured data matrix in this invention to "pre-treat" the training set of ECGs, from which the transformation matrix is derived via simplex optimization, so as to minimize the inherent error in this training set. This is schematically illustrated in FIG. 2. The advantage of AFA is that this technique minimizes predictable error, such as a wandering baseline, baseline noise, and lead placement errors, from a data set, yielded an improved, measured, data set. A comparison of ECG values for lead I as measured and as predicted through AFA is shown in FIG. 3, showing close agreement.

For the purpose of AFA, the ECG can be represented in an n-dimensional system by a linear sum of product terms. The standard 12-lead ECG is a system where n=12. At a particular time t, the 12-lead ECG can be represented as $$V(t)=V_1(t)L_1+V_2(t)L_2+\ldots+V_n(t)L_n,$$

where V is a 12-dimensional vector, $V_m$ is the potential at the $m^{th}$ lead, $L_m$ is a unit vector in the 12-dimensional space, and t is time. The potential V(t) can also be represented by a set of orthogonal basis vectors {X} that spans the space:

$$V(t)=\Sigma^n_{m=1}K_m(t)X_m.$$

Abstract factor analysis identifies n, the number of factors influencing the data set, K, the transformation coefficient matrix, and X, the abstract lead-vector set.

To perform AFA, we consider an N×M data matrix [V] of voltage-time measurements, where N is the number of leads, as indicated in block 105 of FIG. 1, and M is the number of data points. In AFA, a covariance matrix is diagonalized to yield a set of eigenvalues $\lambda_j$ that can be ordered by magnitude. The covariance matrix can be defined as $[Z]=[V]^T[V]$, which is an M×M matrix with up to M eigenvalues, or it can be defined as $[Z]=[V][V]^T$, N×N matrix with up to N eigenvalues. Each eigenvalue $\lambda_j$ corresponds to an orthogonal basis eigenvector $X_j$. The diagonalization procedure involves finding a matrix $[Q_j]$ that diagonalizes [Z]: $[Z][Q_j]=\lambda_j[Q_j]$. In the context of ECGs, M is typically 300 measurements over one complete cycle. Multiple training sets of the N×M matrix are subjected to the AFA technique.

Figure 4:
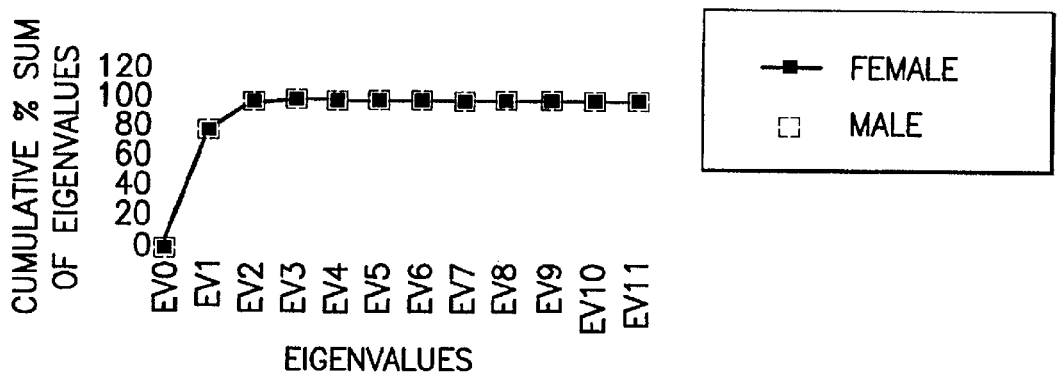
FIG. 4 depicts the cumulative percentage variance as a function of the number of eigenvalues as determined by abstract factor analysis.

From the application of AFA to the data set we find that 3 leads can account for almost all of the information content in an n-lead ECG, where n=12 to 22 leads. This can be demonstrated by means of the cumulative percentage variance. The variance can be defined as:

$$\text{Var}=\lambda_j/\Sigma^n_{k=1}\lambda_k,$$

where n=12 . . . 22 and $\lambda_j$ is the magnitude of the $j^{th}$ eigenvalue. The cumulative percentage variance is defined as $$\text{Cum \% Var}=\Sigma^c_{k=1}\lambda_k/\Sigma^n_{k=1}\lambda_k,$$

where c=$c^{th}$ eigenvalue in the sequence of eigenvalues $\lambda_j$ ordered by magnitude. The cumulative percentage variance is thus a measure of the information content of the system. FIG. 4 is a graph of the cumulative percentage variance as a function of $\lambda_j$ and illustrates that most of the information content of the system is contained in the first 3 eigenvalues. In fact, AFA demonstrates that 3 leads can account for approximately 99% of the information content of a 12-lead ECG. Thus, for a 12-lead system, the resulting transformation matrix [K] is a 3×12 matrix, indicated in block 106 of FIG. 1. Given a set of M voltage-time measurements for 3 leads, the full 12 lead set of measurements can be calculated by multiplying the transformation matrix [K] by the 3×M voltage-time data matrix for the 3 measured leads. This result can easily be generalized to a system with an arbitrary number of leads, hence our n-lead ECG terminology.

The reduction of dimensionality of the factor space of the ECG should not be surprising since the standard 12-lead ECG already has built in redundancy. For example, the measurement of any 2 of the first 6 leads can be used to calculate the other 4 leads according to the following geometrically based formulae:

Lead III=Lead II-Lead I

Lead aVR=-0.87×((Lead I+Lead II)/2)

Lead aVL=0.87×((Lead I-Lead III)/2)

Lead aVF=0.87×((Lead I+Lead III)/2)

Figure 6:
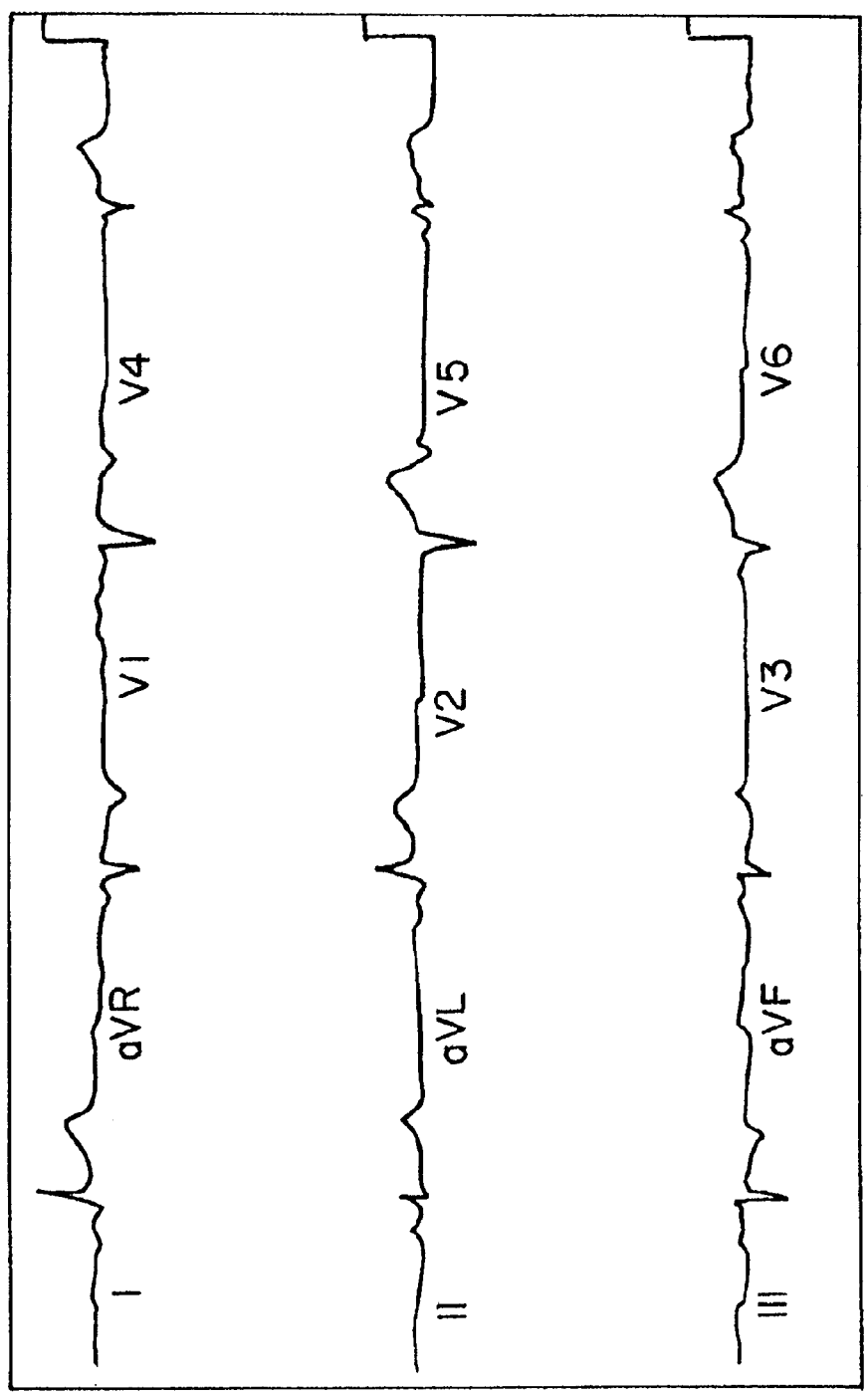
FIG. 6 depicts the graphed output of the usual 12-lead ECG.

The standard 12 lead ECG utilizes 12 PQRST configurations in a format from which the physician makes a diagnosis based on recognizing patterns in the plotted wave forms, as shown in FIG. 6. The ECG in FIG. 6 is the usual and customary 12-lead ECG and is a 12-dimensional representation of 12 voltage-time signals. As stated above, the inventor has verified through the application of AFA that ~99% of the information displayed thereon can be reproduced from the measurement of just 3 leads. Since these leads are approximately orthogonal, they can be plotted against each other in 3-dimensional space, resulting in a spatial ECG loop. Virtually all of the information in a 12-lead ECG is in the 3-dimensional spatial ECG loop. In addition, the inventor has verified that the information content of lead configurations of up to 22 leads can be reproduced from just 3 measured leads. By increasing the lead space to 22 leads, clinicians can more accurately diagnose cardiac pathology, such as right heart infarction or posterior infarction.

Figure 7:
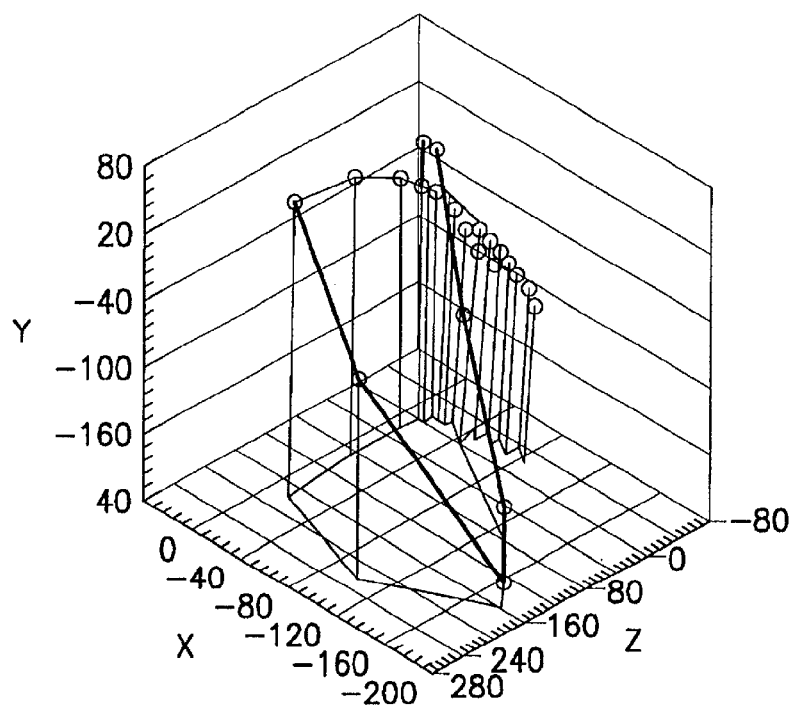
FIG. 7 depicts a normal 3-dimensional spatial ECG loop.
Figure 8:
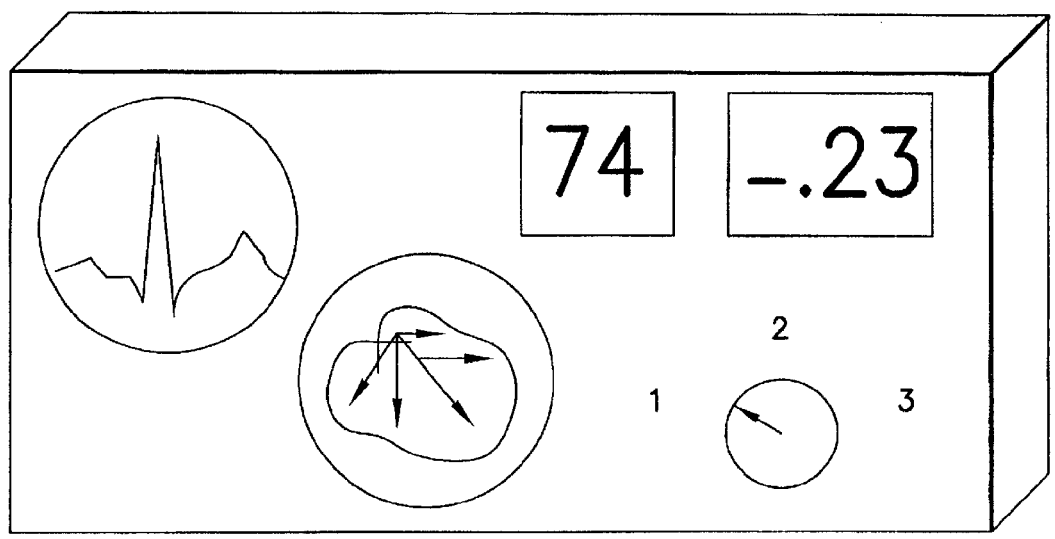
FIG. 8 depicts a portable bedside heart monitor.

A typical 3-dimensional spatial loop for a normal male heart is shown in FIG. 7. This type of display can easily be built into a standard heart monitor, shown in FIG. 8, that incorporates the single wave configuration as currently exists. This spatial loop can also be printed for then patient medical record.

Simplex Optimization

The next step in the derivation of the universal transformation matrix of the present invention was application of the simplex optimization technique ("SOP") to the training set that was subjected to AFA or the measured ECG data, as illustrated in box 107 of FIG. 1. Since 3 leads account for almost all of the information of an n-lead ECG, SOP was applied to a 3-lead set comprised of {I, aVF, V2} to calculate to other leads.

Simplex optimization, which is different from the simplex algorithm used for minimizing constrained linear systems, is a method for finding a maximum for a multiple variable function when the underlying function may be unknown. A simplex is a geometric figure defined by a number of points (n+1) that is one more than the number of variables. For a function of two variables z=f(x, y), one starts with 3 points $\{(x_1,y_1), (x_2,y_2), (x_3,y_3)\}$, and the value of the function is measured for those 3 points. These 3 points are then labeled as "B", "N", and "W", for, respectively, the best, next best (or next worst), and worst values. Since we are seeking a maximum point, the best value has the greatest magnitude.

The next point R for measuring the function f is determined by R=P+(P-W), where P is the centroid of the figure when the worst value point is eliminated.

Once the function has been measured for R, there are 3 possibilities for the next step. First, if the value for R is better than the value for B, an expansion is attempted with a new point defined by E=P+2(P-W). If the value for E is better than B, E is retained and the new simplex is defined by N, B, and E. If the value for E is not better than that for B, the expansion is said to have filed and the new simplex is defined by B, R, and N.

Second, if the value for R is between that for B and N, the new simplex is defined to be B, R, and N, and the process is restarted.

Finally, if the value for R is less desirable than that for N, a step was made in the wrong direction, and a new simplex should be generated. There are 2 possibilities. If the value for R is between that for N and W, the new point should be closer to R than W: $C_R$=P+0.5(P-W), and the new simplex is defined by B, N, and $C_R$. If the value at R is worst than the value at W, then the new point should be closer to W than R: $C_W$=P-0.5(P-W). The new simplex is then defined by B, N, and $C_W$. The process is iterated until a maximum is found.

Figure 16:
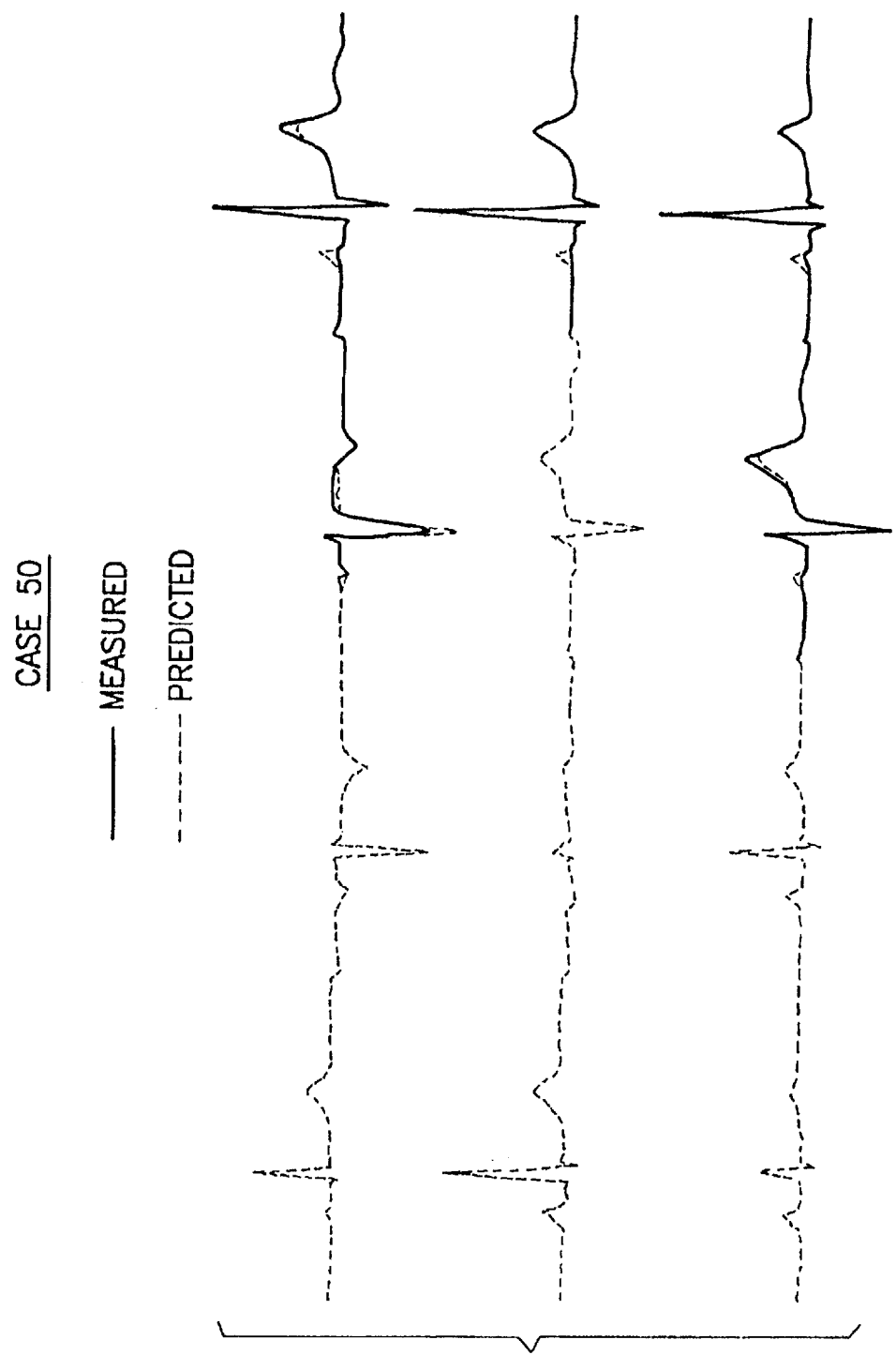
FIG. 16 depicts an ECG printout that compares measured values against values derived through the simplex optimization method.

For the case of the 3-lead ECG, the values of the other leads are calculated as functions of a 3-lead set, preferably {I, aVF, V2}. Thus, the simplex will be a 3-dimensional figure defined by 4 points that represent the starting values of {I, aVF, V2}. The results of this optimization were used to define an N×3 universal transformation matrix [K] such that when multiplied by a vector comprising the 3 leads {I, aVF, V2} for a particular time yield a full n-lead ECG, as illustrated in block 108 of FIG. 1. In particular, the [K] matrix was calculated for the full PP cycle of the heart beat as well for segments within the PP cycle, such as the PR interval, the QRS interval, the SP interval, and the QT interval. The accuracy of the optimization was validated by comparing the derived values for the II, III, aVR, and aVL leads with measured values for those leads. A comparison of a synthesized ECG based on values derived from simplex optimization with a measured ECG is depicted in FIG. 16.

Body Surface Maps

Figure 12:
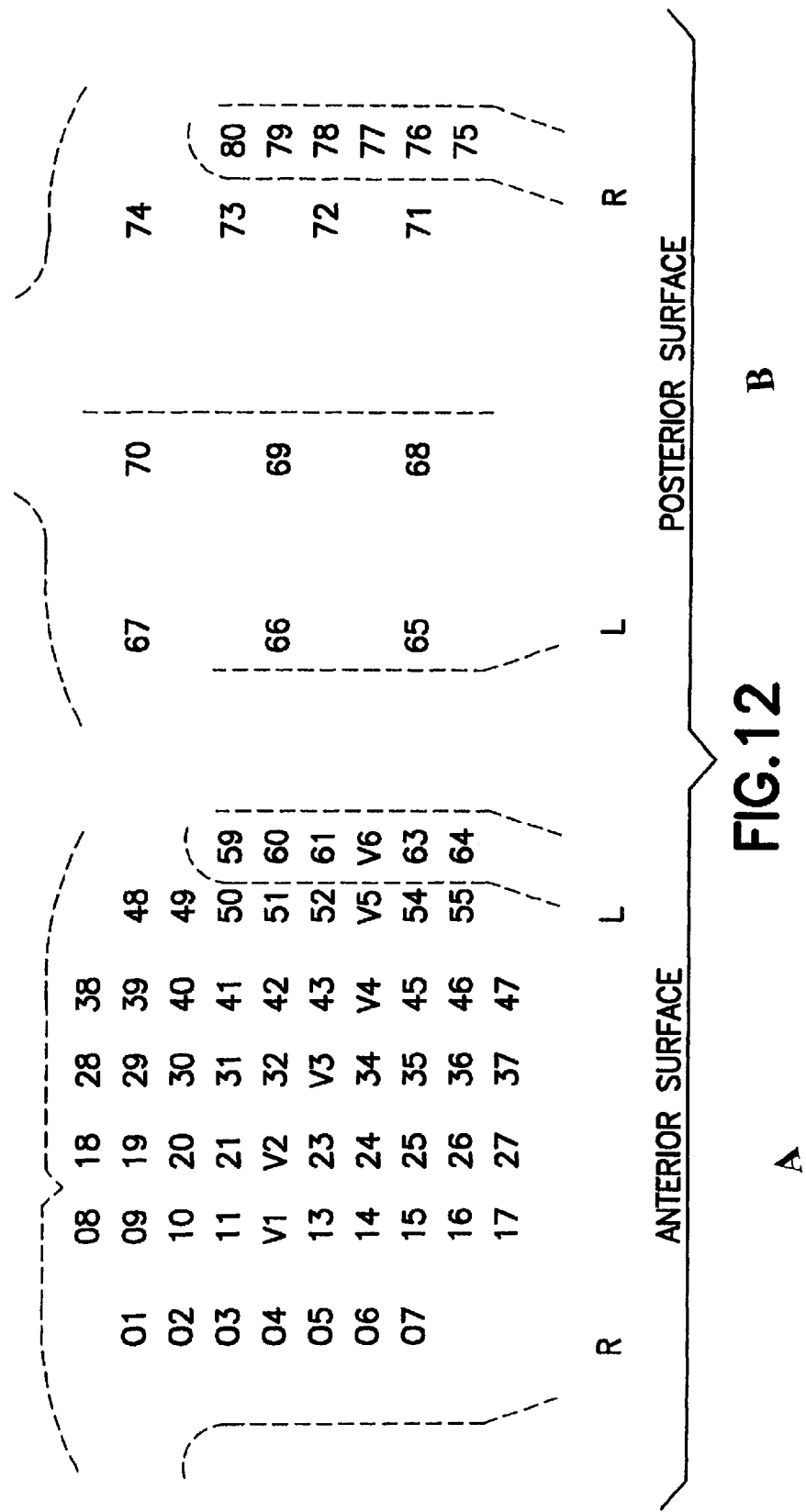
FIG. 12a depicts the anterior view of chest lead placements of an 80-electrode vest for generating a body-surface voltage map.
FIG. 12b depicts the posterior view of chest lead placements of an 80-electrode vest for generating a body-surface voltage map.
Figure 13:
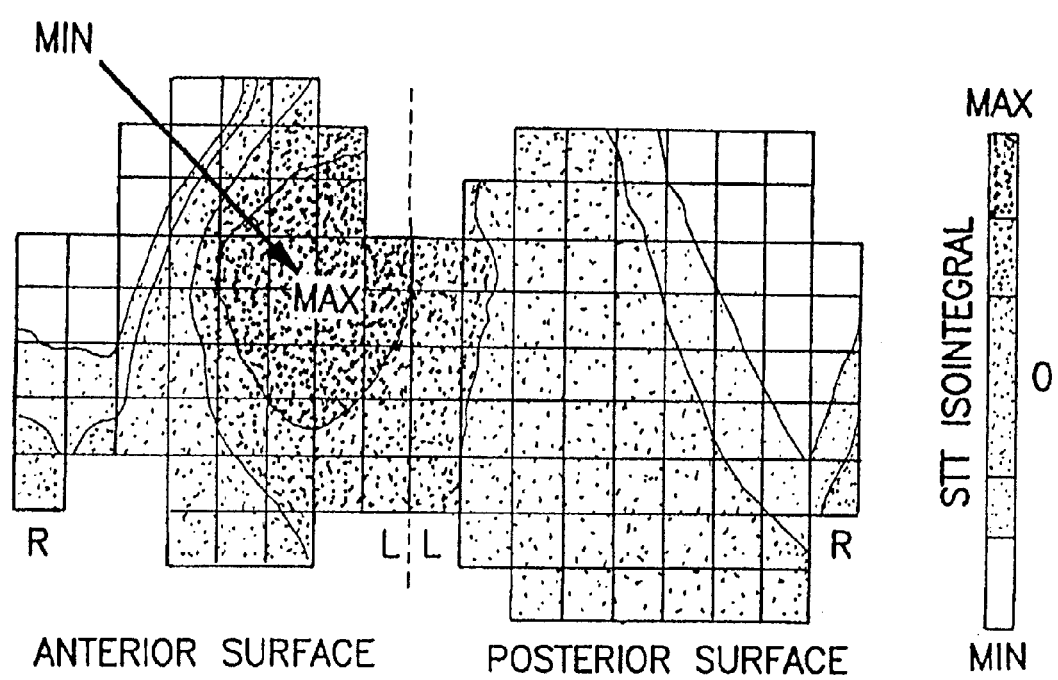
FIG. 13 depicts an unwrapped body surface map as if hinged on the left lateral side.
Figure 14:
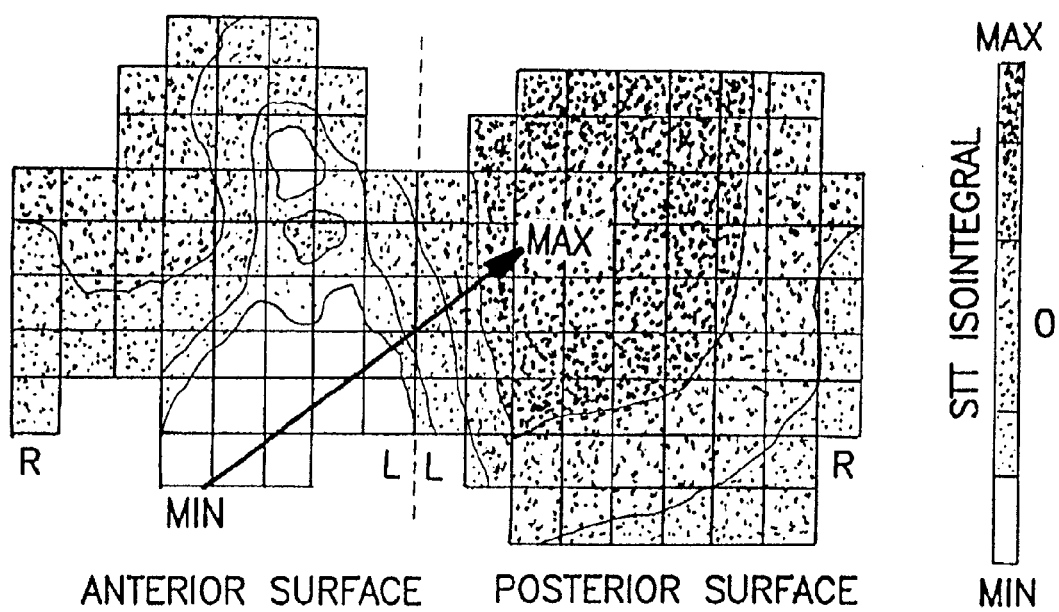
FIG. 14 depicts the body surface map of a patient with acute MI.

As described above, the current n comprises up to 22 leads placed around the body torso. Although the inventor has increased n from 12 to 22 leads, it is possible to use the method of the invention to derive more than 22 leads. By plotting the voltage-time data of multiple leads in a contour graph, a body surface map ("BSM") can be visualized. FIGS. 12a and 12b depict the chest lead placements from one electrode system soon to be commercial available. This system incorporates the placement of an 80 electrode vest around a patient's chest for voltage-time acquisition. A BSM of a patient derived from such a configuration is displayed in FIG. 13. This figure uses a color-coded contour drawn unwrapped as if hinged on the left lateral side so that the posterior surface is displayed in continuity next to the anterior surface. FIG. 14 displays a BSM measured from the end of the S-segment of the PQRST wave to the end of the T-segment ("ST-T"), in a patient with acute myocardial infarction ("MI") whose 12-lead scalar ECG showed only a depression in the ST portion of the PQRST wave. The BSM demonstrates a large posterior red area (indicated by the arrow in the figure) that indicates a posterior MI.

Figure 15:
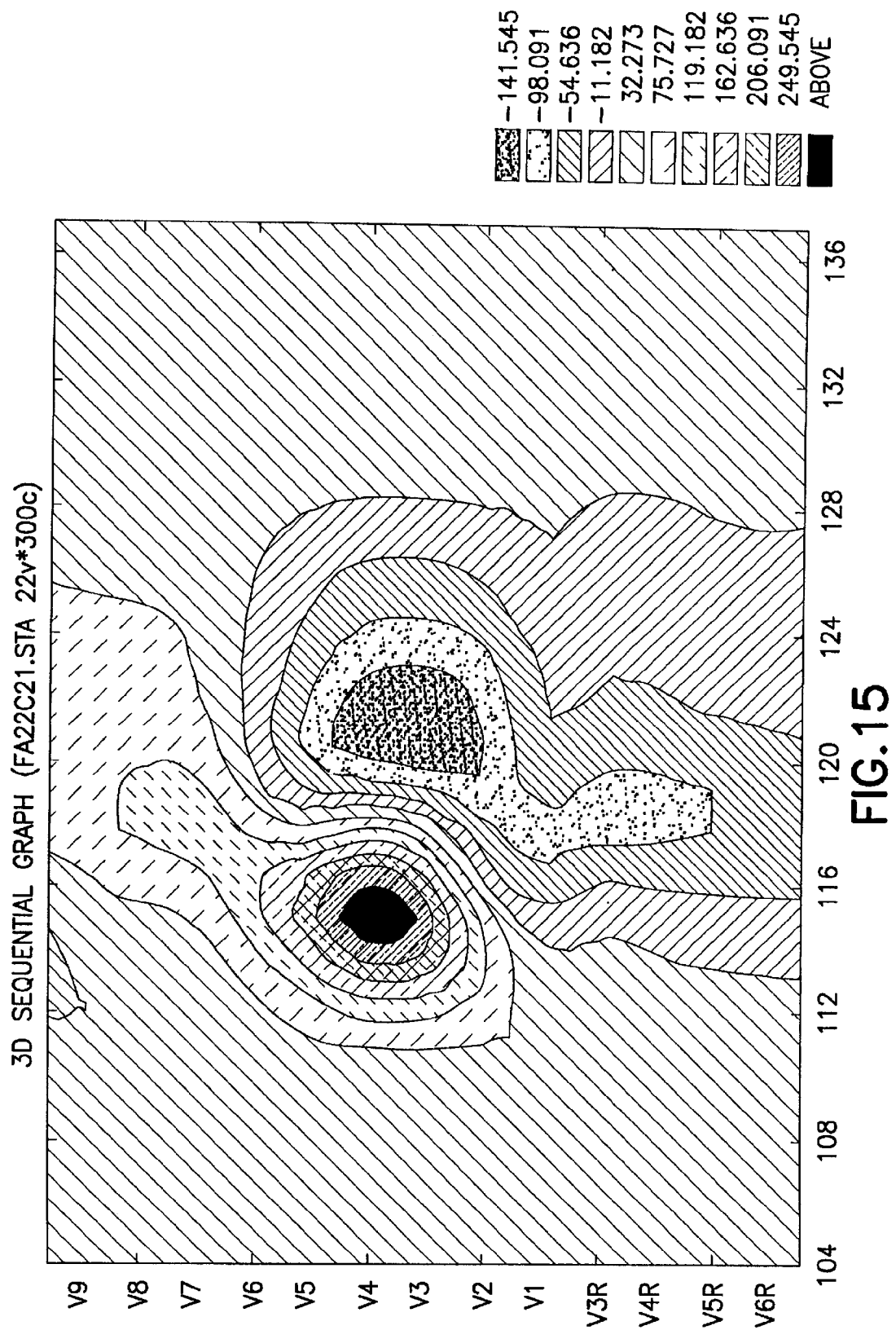
FIG. 15 depicts the body surface map of a patient as calculated from the application of the universal transformation matrix of the invention to a 3 lead system.

The cost of the numerous leads required for a BSM and the time it takes to place the leads make BSMs prohibitive for application in an acute care setting. Sophisticated software and hardware is also required to analyze the BSM data, although recent technological advances make this process less cumbersome. However, BSMs are now easily achievable using the method of the present invention, as any number of leads can be derived from just 3 measured leads using the universal transformation matrix of the present invention. A BSM derived from a 3-lead system is displayed in FIG. 15.

Clinical Significance of Eigenvalues

Another clinical application of the method of the invention is that the cumulative percentage sum of the eigenvalues calculated from AFA demonstrate statistically significant differences between normal and MI ECGs. Thus, the eigenvalue contribution to the information space of the ECG is a marker for MI. In particular, by tracking the change in eigenvalue magnitudes over successive ECGs, a clinician can predict the onset of MI in a patient.

Figure 17A:
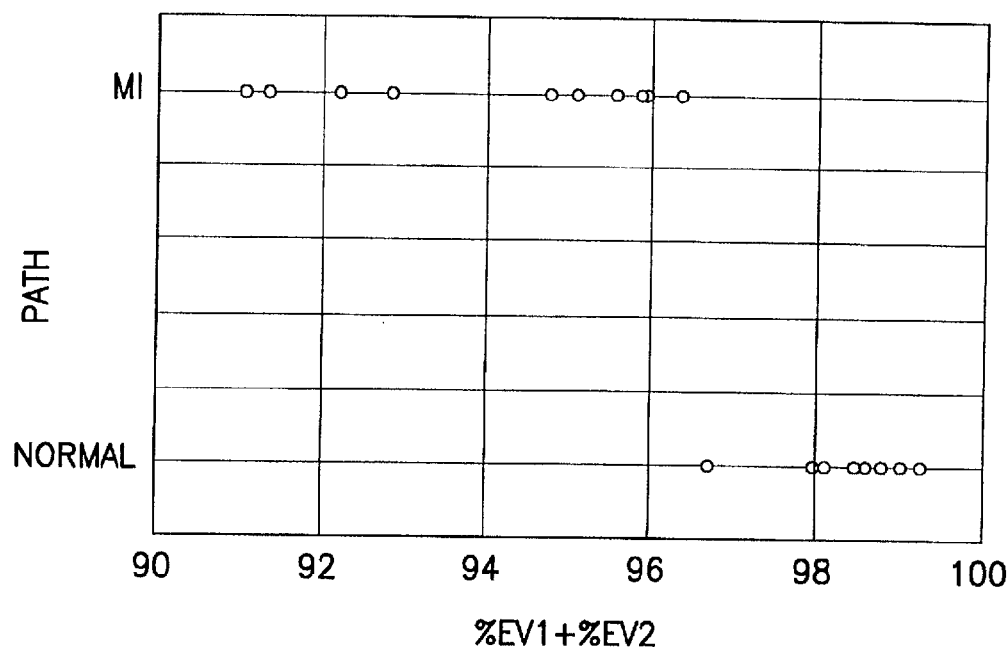
FIGS. 17a and 17b depict plots of normal eigenvalues vs. MI eigenvlaues in an 8-lead ECG.
Figure 17B:
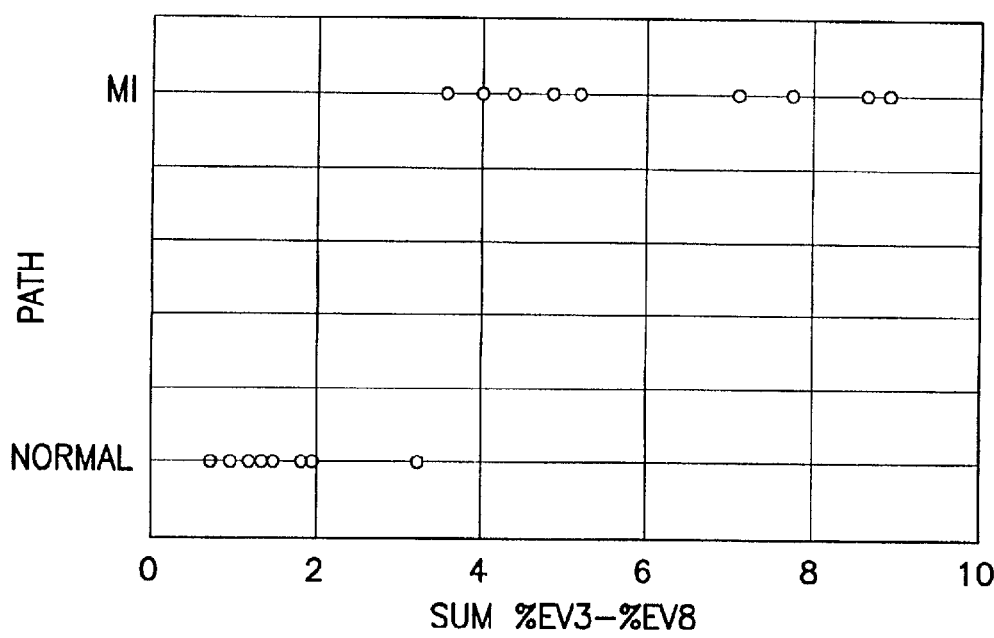

In a study involving 20 patients, 10 men and 10 women, wherein half of each group displayed normal heart function and the other half of each group exhibited MI, and in which an 8-lead ECG was used, it was found that the two largest eigenvalues decreased in magnitude in going from normal heart function to MI, while the 6 smallest gained in magnitude. Although the decrease in magnitude of the two largest was not statistically significant, the increase in magnitude of the 6 smallest was statistically significant. FIG. 17a depicts a plot of the cumulative percentage sum of the normal and MI eigenvlaues for the two largest eigenvalues, here denoted by EV1 and EV2. The plot displays a sharp break between the MI eigenvalues and the normal eigenvalues, wherein for normal function, this cumulative sum is greater than 97% of the total sum, while for MI the cumulative sum is less than 97% of the total value. More importantly, since these differences are statistically significant, the cumulative sum of the 6 smallest eigenvalues, here denoted by EV3 to EV6, shows a break between MI eigenvalues and normal eigenvalues. This is depicted in FIG. 17b. As can be seen from the figure, the cumulative sum of the MI values range from about 3% up to about 9% of the total sum, while the cumulative sum of the normal values is less than 3% of the total sum.

This has great clinical implications. As of the current time, the only markers for MI are measured through blood testing. This takes time, and has an associated cost. These blood test measurements are also NOT performed in real time. They are ordered by the physician when needed, but it takes time for the technician to arrive and take the blood sample from the patient. It is just not feasible to perform such chemical testing every 1–15 minutes. The eigenvalues of the ECG can now be measured on a beat to beat basis using a 3-lead bedside monitor, in real time, on demand, without the need of a technician. This invention would allow the immediate derivation of an n-lead ECG (e.g., 12-lead ECG) from a 3-lead monitor from which the eigenvalues can be calculated instantaneously. The eigenvalue percentage contribution is itself a marker for MI. This can be displayed along with the heart rate on any customary bedside monitor. Because this eigenvalue marker can be calculated on a beat-to-beat basis in less than a second with current conventional computer technology, the variability of the eigenvalues in time, and the rate of change of the eigenvalues, either by magnitude or percent contribution, are also markers for acute MI. This invention would allow the first known real-time electrophysiologic marker for acute MI. Naturally, any function utilizing the eigenvalues would accomplish the same purpose.

The method of the invention can be implemented on any computer system using any available programming language. One embodiment of the invention is implemented using Microsoft Visual Basic executing on a personal computer running the Windows operating system. The invention is not limited to this implementation, however, and implementations is other programming languages executing on other machines, such as the Mackintosh, or workstations running under the Unix operating system or variants thereof, such as Linux, are within the scope of the invention.

While the present invention has been described and illustrated in various preferred and alternate embodiments, such descriptions and illustrations are not to be construed to be limitations thereof. Accordingly, the present invention encompasses any variations, modifications and/or alternate embodiments with the scope of the present invention being limited only by the claims which follow.

What is claimed is:

1. A method for synthesizing electrocardiogram leads-comprising the steps of:
   (a) calculating a univeral transformation matrix by
      obtaining a sequence of voltage-time measurements for a full set of n-lead electrocardiogram leads for a given n;
      measuring the voltage-time measurements of the full set of n-lead electrocardiogram leads; and
      performing simplex optimization on the full set of the voltage-time measurements for an n-lead electrocardiogram to obtain the universal transformation matrix; and (b) multiplying the universal transformation matrix by a minimal subset of the voltage-time measurements to calculate the full set of voltage-time measurements in the n-lead electrocardiogram.

2. The method of claim 1, further comprising the steps of subjecting the sequence of voltage-time measurements to abstract factor analysis to obtain a set of eigenvalues and associated eigenvectors; and identifying the minimal subset of electrocardiogram leads from which the full set of voltage-time measurements can be calculated with acceptable error.

3. The method of claim 2, further comprising the step of tracking functions of eigenvalues for successive voltage-time measurements in order to predict the onset of pathology, including myocardial infarction.

4. The method of claim 1, further comprising the step of calculating any segment of a cardiac cycle from the universal transformation matrix as applied to the minimal subset of electrocardiogram leads.

5. The method of claim 1, wherein the full set of electrocardiogram leads can comprise from 12 to at least 22 leads.

6. The method of claim 1, wherein the minimal subset of electrocardiogram leads comprises 3 leads.

7. The method of claim 6, wherein the 3 leads are the I, aVF, and V2 leads.

8. The method of claim 6, wherein the 3 leads are the I, II, and V2 leads.

9. The method of claim 6, wherein the 3 leads are the I, aVF, and V9 leads.

10. The method of claim 6, wherein the 3 leads are the I, II, and V9 leads.

11. The method of claim 1, further comprising the step of constructing a body surface map from the calculated full set of voltage-time measurements.

12. The method of claim 1, wherein the full set of electrocardiogram leads can comprise up to 80 or more leads, and further comprising the step of constructing a body surface map from this full set of voltage-time measurements.

13. The method of claim 1, using the technique of cumulative percentage variance to identify the minimal subset of electrocardiogram leads.

14. The method of claim 1, using any 3 measured leads of a conventional n-lead electrocardiogram to derive the complete electrocardiogram.

15. A method for synthesizing electrocardiogram leads comprising the steps of:

obtaining a sequence of voltage-time measurements for a full set of from 12 to at least 22 electrocardiogram leads;

measuring the voltage-time measurements of the full set of n-lead electrocardiogram leads;

subjecting the sequence of voltage-time measurements to abstract factor analysis to obtain an improved full set of n-lead electrocardiogram leads;

using cumulative percentage variance to identify a minimal subset of 3 electrocardiogram leads from which the synthesized full set of n-lead voltage-time measurements can be calculated with acceptable error;

performing simplex optimization on the improved full set of voltage-time measurements for an n-lead electrocardiogram to obtain a universal transformation matrix; and multiplying the universal transformation matrix by the minimal subset of the voltage-time measurements to calculate the full set of voltage-time measurements in the n-lead electrocardiogram.

16. The method of claim 15, further comprising the step of calculating any segment of a cardiac cycle from the universal transformation matrix as applied to the minimal subset of electrocardiogram leads.

17. The method of claim 15, wherein the 3 leads are the I, aVF, and V2 leads.

18. The method of claim 15, wherein the 3 leads are the I, II, and V2 leads.

19. The method of claim 15, wherein the 3 leads are the I, aVF, and V9 leads.

20. The method of claim 15, further comprising the step of constructing a body surface map from the calculated full set of voltage-time measurements.

21. The method of claim 15, wherein the full set of electrocardiogram leads can comprise up to 80 or more leads, and further comprising the step of constructing a body surface map from this full set of voltage-time measurements.

22. The method of claim 15, using any 3 measured leads of a conventional n-lead electrocardiogram to derive the complete electrocardiogram.

23. The method of claim 15, further comprising the step of tracking functions of eigenvalues for successive voltage-time measurements in order to predict the onset of pathology, wherein said pathology includes myocardial infarction.

24. The method of claim 15, wherein the 3 leads are the I, II, and V9 leads.

* * * * *